(12) United States Patent
Munro, III et al.

(10) Patent No.: US 6,527,693 B2
(45) Date of Patent: Mar. 4, 2003

(54) METHODS AND IMPLANTS FOR PROVIDING RADIATION TO A PATIENT

(75) Inventors: John J. Munro, III, North Andover, MA (US); Anthony J. Armini, Manchester, MA (US)

(73) Assignee: Implant Sciences Corporation, Wakefield, MA (US)

( * ) Notice: Subject to any disclaimer, the term of this patent is extended or adjusted under 35 U.S.C. 154(b) by 8 days.

(21) Appl. No.: 09/772,765

(22) Filed: Jan. 30, 2001

(65) Prior Publication Data

US 2002/0103410 A1 Aug. 1, 2002

(51) Int. Cl.⁷ .................................................. A61N 5/00
(52) U.S. Cl. .............................................. 600/3; 600/1
(58) Field of Search ............................. 600/1, 2, 3, 4, 600/5, 6, 7, 8, 9, 10

(56) References Cited

U.S. PATENT DOCUMENTS

| | | | | |
|---|---|---|---|---|
| 4,323,055 A | * | 4/1982 | Kubiatowicz | 128/1.2 |
| 4,510,924 A | * | 4/1985 | Gray | 128/1.2 |
| 4,763,642 A | * | 8/1988 | Horowitz | 128/1.2 |
| 4,784,116 A | * | 11/1988 | Russell, Jr. et al. | 128/1.2 |
| 4,891,165 A | * | 1/1990 | Suthanthiran | 252/633 |
| 4,946,435 A | * | 8/1990 | Suthanthiran et al. | 600/3 |
| 4,994,013 A | * | 2/1991 | Suthanthiran et al. | 600/8 |
| 5,405,309 A | * | 4/1995 | Garden, Jr. | 600/3 |
| 5,616,114 A | * | 4/1997 | Thornton et al. | 600/3 |
| 5,912,225 A | | 6/1999 | Mao et al. | 514/2 |
| 6,010,445 A | * | 1/2000 | Armini et al. | 600/3 |
| 6,059,714 A | | 5/2000 | Armini et al. | 600/3 |
| 6,060,036 A | | 5/2000 | Armini | 424/1.29 |
| 6,066,856 A | * | 5/2000 | Fishman | 250/519.1 |
| 6,077,213 A | * | 6/2000 | Ciezki et al. | 600/3 |
| 6,083,148 A | * | 7/2000 | Williams | 600/2 |
| 6,099,457 A | * | 8/2000 | Good | 600/8 |
| 6,099,458 A | * | 8/2000 | Robertson | 600/8 |
| 6,143,431 A | * | 11/2000 | Webster | 428/669 |
| 6,163,947 A | | 12/2000 | Coniglione | 29/458 |
| 6,166,184 A | | 12/2000 | Hendriks et al. | 530/356 |
| 6,168,777 B1 | | 1/2001 | Greff et al. | 424/1.25 |
| 6,183,409 B1 | * | 2/2001 | Armini | 600/3 |
| 6,248,057 B1 | * | 6/2001 | Mavity et al. | 600/3 |
| 6,264,598 B1 | * | 7/2001 | Armini | 600/3 |
| 6,400,796 B1 | * | 6/2002 | Munro, III et al. | 378/64 |

FOREIGN PATENT DOCUMENTS

| | | |
|---|---|---|
| WO | WO 98/44020 | 10/1998 |
| WO | WO 98/46286 | 10/1998 |
| WO | WO 00/19976 | 4/2000 |

* cited by examiner

*Primary Examiner*—Henry C. Yuen
*Assistant Examiner*—Frederick Nicolas
(74) *Attorney, Agent, or Firm*—Foley Hoag LLP

(57) ABSTRACT

This application relates to devices and methods for locally delivering therapeutic radiation to tissue in the body of a patient. In certain embodiments, the subject devices are implanted into a cavity in the patient left by surgical removal of tumorous tissue or other diseased tissue, to deliver radiation to the tissue surrounding the cavity. In certain embodiments, the devices are elastic or can otherwise be shaped to conform to the shape of the cavity in the patient.

30 Claims, 2 Drawing Sheets

Treatment Device

Treatment Device

METHODS AND IMPLANTS FOR PROVIDING RADIATION TO A PATIENT

FIELD OF THE INVENTION

The present invention relates generally to therapeutic radioactive implants and methods of use thereof, and more particularly to radioactive devices for implantation into a cavity of a patient's body and methods of use thereof.

BACKGROUND OF THE INVENTION

Gross surgical removal of tumorous tissue can leave behind traces of tumorous, precancerous, or other diseased tissue which can foster recurrence or metastasis of the tumor. Accordingly, the site of removal of a tumor is often treated postoperatively in an attempt to destroy any such diseased tissue left behind by the surgery. Conventional techniques for treating the site of surgical removal of a tumor include post-operative administration of radiation, chemotherapy, and/or heat.

Currently, external beam therapy and short-range therapy are two commonly practiced techniques for administration of post-operative radiation. In external beam therapy, also known as teletherapy, an external radiation beam is directed at the treatment site. In teletherapy, the radiation beam must be carefully positioned with respect to the treatment site to minimize the radiation exposure of the surrounding healthy tissue. Even with a high degree of precision, however, healthy tissue in the vicinity of the treatment site may receive significant doses of radiation. This side effect can be compounded when treatment requires repeated administrations, each requiring careful positioning of the radiation beam.

In short-range therapy, also known as brachytherapy, radioactive sources are placed at or near the treatment site to provide site-specific delivery of radiation therapy, potentially reducing undesirable side effects associated with teletherapy, such as irradiation of healthy tissue. A common brachytherapy technique uses catheters to deliver radiation to the treatment site. In this technique, numerous catheters may be simultaneously inserted into the treatment site, sewn into place, loaded with solid isotopic pellets for a prescribed time, and then removed. The process of placing a number of catheters simultaneously within the appropriate region is cumbersome and time-intensive. Additionally, invasive insertion and external exposure of the catheters presents an increased risk of infection to the patient, and can result in significant discomfort for the patient during treatment. Finally, any subsequent treatment, for example, treatment following tumor recurrence, requires that the entire process be repeated from the beginning.

Another common brachytherapy technique employs radioactive implants to deliver radiation therapy. In this technique, numerous radioactive pellets or seeds are implanted directly into the treatment site. Several varieties of radioactive seeds are currently available, including cylinders that contain radioactive sources and bodies that include radioactive layers. However, the radiation fields generated by the implants are typically highly non-uniform, resulting in highly non-uniform distributions of radiation dose across the treatment site. Also, the seeds are not typically implanted in the cavity formerly occupied by the bulk of the tumor at the time of excision, thus generally requiring further surgical incisions. Lastly, the seeds are typically made of materials that do not conform to the outline of the cavity to be treated, thereby reducing the therapeutic efficiency of the implants.

A device for providing radiation treatment to a treatment site that can be implanted at the time of tumor removal and which delivers a more uniform dose of radiation throughout the surrounding tissue would be desirable.

SUMMARY OF THE INVENTION

In accordance with one embodiment, the present invention is directed to a device for the administration of radiation to tissue adjacent a cavity wall. The device includes an outer portion that has a size sufficient for implantation adjacent the cavity wall of a cavity, e.g., of a size sufficient to substantially fill the volume of the cavity. The outer portion may be made of a biocompatible material having low radiation absorption, to facilitate transmission of radiation to the tissue adjacent the cavity wall. The outer portion may be made of an elastic biocompatible material, so that the outer portion conforms to a contour of the cavity wall to provide close approximation to the tissue therealong. The device further includes at least one radioactive source. The radioactive source may be encapsulated by the outer portion, e.g., positioned in an area spatially located from a periphery of the outer portion. A radioactive source may be a radioactive nuclide that decays by electron capture, without the emission of beta particles. Such a radioactive nuclide may decay with the emission of X-rays, for example, having a weighted average energy from about 20 keV to about 100 keV. The radioactive nuclide may be selected from palladium-103, iodine-125, gadolinium-153, samarium-145, and ytterbium-169.

In accordance with another embodiment, the present invention includes a method for the treatment of tissue adjacent a cavity wall. Such a method may include identifying a cavity within a body of tissue, e.g., by removing a portion of tumorous tissue within a body of tissue so as to generate a cavity. The method also includes placing within the cavity a device, such as described above, having an outer portion and at least one radioactive source, e.g., in which the outer portion has a size sufficient for implantation adjacent the cavity wall, and the radioactive source is positioned within an area spatially located from a periphery of the outer portion for delivering radiation therapy to the tissue adjacent the cavity wall.

The present invention also provides methods for manufacturing devices, such as described above, useful in the methods disclosed herein.

Further features and advantages of the present invention will become apparent from the following description of embodiments and from the claims.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

DETAILED DESCRIPTION OF THE INVENTION

The description below pertains to several illustrative embodiments of the invention. Although many variations of the invention may be envisioned by one skilled in the art, such variations and improvements are intended to fall within the compass of this disclosure. Thus, the scope of the invention is not to be limited in any way by the disclosure below.

Figure 1:
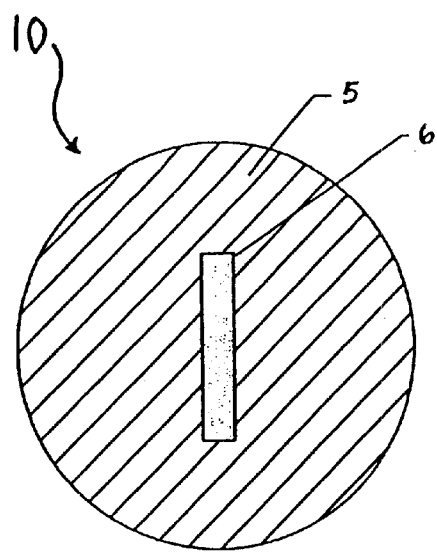
FIG. 1 represents a treatment device according to the present invention.
Figure 2:
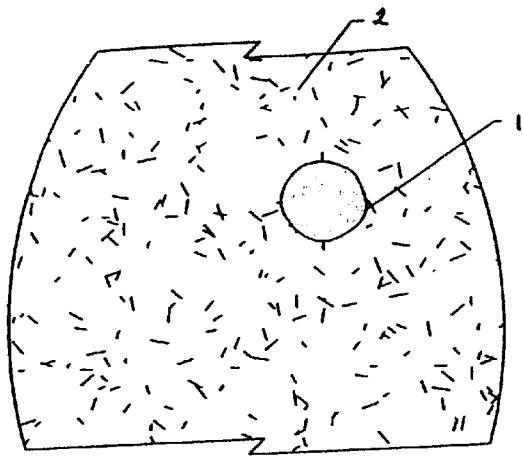
FIG. 2 illustrates tumorous tissue within a body of tissue.
Figure 3:
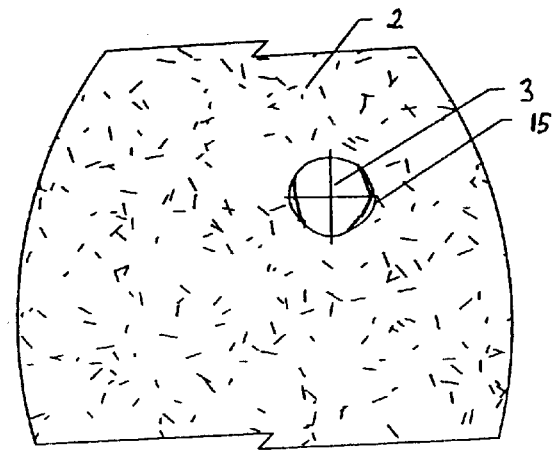
FIG. 3 depicts the body of tissue with most of the tumorous tissue removed.
Figure 4:
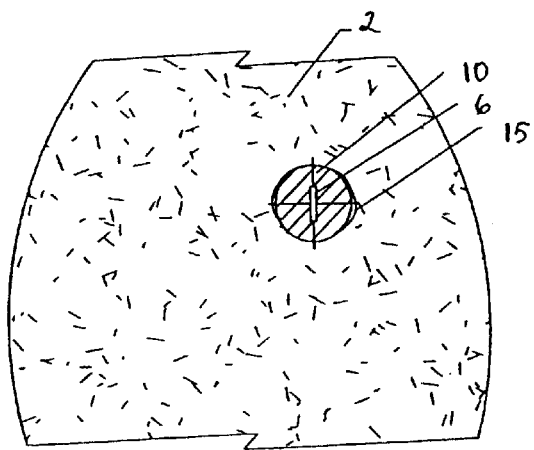
FIG. 4 shows a therapeutic device according to the present invention implanted into the cavity formerly occupied by the tumorous tissue.

The present invention relates to devices and methods for delivering therapeutic radiation to a patient. One embodiment of the present invention provides a device 10, as shown in FIG. 1, including an outer portion 5 and a radioactive source 6. In an exemplary method according to the present invention, tumorous tissue 1 in a region of healthy tissue 2, as shown in FIG. 2, is removed to form a cavity 3 which may include residual diseased tissue 15, as shown in FIG. 3. The tumorous tissue 1 may be any cancerous tissue, precancerous tissue, or hyperproliferative tissue, including any type of tumor, such as an ovarian, breast, lung, colon, liver, brain, stomach, or other tumor. Healthy tissue 2 may be any type of living tissue. As shown in FIG. 4, a device 10 may be implanted in the cavity 3 to deliver radiation to adjacent residual diseased tissue 15. The device 10 may be placed in the cavity substantially immediately after removing the tumorous tissue 1, e.g., prior to closing the incision through which the tumorous tissue 1 was removed.

The outer portion 5 of a device 10 may be formed from any material suitable for use in medical devices, particularly in implantable medical devices. The outer portion may be biocompatible, e.g., comprising materials that do not induce a toxic or allergic reaction when contacted with living tissue, or may be coated with a biocompatible coating. Suitable biocompatible materials include silicone polymers, organic polymers, titanium, carbon, stainless steel, tantalum, hafnium, zirconium, and combinations thereof.

The outer portion 5 preferably has a size of at least about one centimeter in average diameter, e.g., from one to five centimeters in average diameter. For example, the outer portion 5 may be of a size sufficient to substantially occupy the volume of the cavity, such as a size approximately equal to the size of a cavity left by removal of a tumor. Although the outer portion 5 may be of any shape, the shape is preferably rounded or spheroidal, so that the distribution of radiation emitted from the device 10 is substantially equal over the surface of the device 10, e.g., similar to a uniform point source of radiation.

The outer portion 5 may be constructed of a material that can conform to the shape of the cavity where the device 10 is to be implanted to enhance the efficacy of the radiation therapy. Preferably, the outer portion 5 comprises or consists essentially of an elastic material, whereby the outer portion 5 can be shaped to conform along a contour of the cavity 3 to provide close approximation to the tissues 2, 15 therealong. In certain embodiments, the outer portion may conform to all, substantially all, or a substantial portion of the wall of the cavity 3. Suitable elastic materials include silicone polymers and organic polymers.

Generally, the material comprising the outer portion 5 will absorb a portion of the radiation emitted by the radioactive source 6, thereby diminishing the amount of radiation delivered to the tissue 15 surrounding the device 10. The amount of absorption is related to the thickness and composition of the outer portion 5. The outer portion 5 is preferably thin enough to transmit most of the radiation generated by the radioactive source 6, but thick enough to impart sufficient mechanical strength to the device 10. Preferably, the outer portion 5 comprises or consists essentially of one or more materials which exhibit low radiation absorption, even more preferably a low-density material, e.g., materials consisting essentially of elements having atomic numbers in the range of about 1 to about 40, such as silicone polymers or organic polymers (e.g., cross-linked or non-cross-linked). In certain embodiments, an organic polymer included in the outer portion 5 is substantially non-biodegradable, e.g., does not significantly disintegrate or degrade during long-term implantation in a biological tissue, in order to protect the radioactive source from biological tissues and vice versa. Examples of substantially non-biodegradable organic polymers include, for example, Teflon, cellulose acetates (including cellulose diacetate), ethylene vinyl alcohol copolymers, hydrogels (e.g., acrylics), polyacrylonitrile, polyvinylacetate, cellulose acetate butyrate, nitrocellulose, polypropylene, polyethylene terephthalate, nylon, polyurethane, polyphenylene oxide blends, polyphenylsulfone, polysulfone, polyether sulfone, polyphenylene sulfide, phenyletheretherketone, polyetherimide liquid crystal polymer, copolymers of urethane/carbonate, copolymers of styrene/maleic acid, and mixtures thereof. In embodiments wherein the radioactive source is coated with a substantially non-biodegradable biocompatible layer, however, the outer layer may comprise or consist essentially of a biodegradable organic polymer, to permit gradual healing of the site of removal of a tumor. Representative biodegradable polymers include polylactide, polyglycolide, polycaprolactone, polycarbonate, poly(phosphoesters), polyanhydride, polyorthoesters, and natural polymers such as alginate and other polysaccharides including dextran, cellulose, collagen, and chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins. Various polymers suitable for use in the devices and methods of the present invention are discussed in greater detail in U.S. Pat. Nos. 5,912,225, 6,168,777, 6,166,184, and 6,163,947, and International applications WO 98/46286, WO 98/44020, WO 98/44021, WO 00/19976, and references cited therein.

The radioactive source 6 delivers radiation to the tissues 2, 15 surrounding the cavity 3, and is preferably encapsulated, e.g., surrounded, by the outer portion 5. Even more preferably, the radioactive source 6 is located at or near the center of the outer portion 5, so that the distribution of radiation emitted from the device 10 is substantially equal over the surface of the device 10, e.g., similar to a uniform point source of radiation.

The radioactive source 6 may be of any shape, although preferably substantially spheroidal, and may comprise one or more radioactive nuclides. The desired radiation dosage and the absorptivity of the material comprising the outer portion 5 may be considered in determining the types and quantities of nuclides to be included in the radioactive source 6. Generally, the choice of a nuclide for providing radiation therapy depends on the half-life of the nuclide and the total radiation dosage desired, as is known to those of ordinary skill in the art. In certain embodiments, nuclides in the radioactive source 6 may decay by electron capture, and may additionally decay substantially without beta emission. For example, such nuclides may emit greater than 95% of their radiation in low energy X-rays, e.g., having energies between about 20 keV and about 100 keV. Preferred nuclides comprise palladium-103, iodine-125, gadolinium-153, samarium-145, and ytterbium-169, and any combination thereof, although other nuclides, such as 32P, 32S, 186Re, 188Re, 90Y, 187W, 131Cs, or any other therapeutic radionuclide known in the art, may be employed.

The radioactive source 6 may consist essentially of the therapeutic radionuclide, or may comprise one or more additional materials. For example, the radionuclide may be associated with a body comprising one or more additional materials. The term "associated with" is used herein to describe the relationship between a body and a radioisotope or precursor, including relationships such as infusion, coating, mixture, incorporation, interleaving, envelopment, embedding, diffusion, enclosure, adhesion, imprinting, deposition, electroplating, implantation, and melding of one or more elements with one or more other elements, or any other relationship that implies permanence or semi-permanence of that relationship. A body may comprise any suitable material, such as metals and metal alloys, organic polymers, and ceramic oxides. Suitable metals and metal alloys comprise, for example, stainless steel, rhodium titanium, chromium, nickel, nitinol, rhenium, and rhenium alloys. Preferred materials comprise stainless steel, rhodium, nitinol, titanium, palladium, and alloys thereof.

In certain embodiments, a device 10 may be prepared from a device comprising a non-radioactive precursor disposed in an outer layer 5, by exposing the non-radioactive precursor to a source of thermal neutrons to activate the non-radioactive precursor to a radioactive source 6. Suitable non-radioactive precursor isotopes include ytterbium-168, xenon-124, palladium-102, phosphorous-31, barium-130, yttrium-89, rhenium-185, rhenium-187, and tungsten-186. The criteria for selection of a stable precursor isotope that is to be neutron-activated may include: having a half-life between about two and about thirty days, or between about two and about seventy days; having a high neutron activation cross-section; and having the resultant radioisotope primarily emit beta particles or x-rays rather than gamma rays. Beta particles and x-rays provide a short-range dose to tissue, and thus limit the exposure of healthy tissues to the radiation.

When the medical device body is thermal neutron-activated, both the precursor isotope and any activatable isotopes in the body may become radioactive. If the quantity or neutron activation cross-section of a precursor isotope is increased, the required level of the radioactive isotope can be obtained with less neutron activation time. Additionally, the body may consist essentially of materials, such as stainless steel, chromium, or nickel, that do not become substantially radioactive when exposed to a source of thermal neutrons.

The amount of exposure required for neutron activation of the medical device depends on the flux rate of the nuclear reactor used, the thickness and composition of the coating applied to the body, the neutron activation cross-section of the precursor element, and the amount of beta radiation desired. The exposure time could range from a few minutes in a very high flux reactor to several hours in a low flux reactor.

In embodiments wherein the outer portion 5 comprises a biodegradable material, the radioactive source 6 (or an activatable precursor thereof) preferably has a non-biodegradable biocompatible layer disposed thereon, so that upon degradation of the outer layer 5, the radioactive source 6 remains protected by a biocompatible layer.

For additional background on radioactive implants and methods for producing them, see U.S. Pat. Nos. 6,060,036 and 6,059,714, and U.S. patent application Ser. Nos. 09/366, 022 and 09/247,198.

EXEMPLIFICATION

The following example illustrates a particular embodiment of the devices and methods described herein without limiting the scope of the invention in any way. Those of skill in the art will recognize a wide array of variations and modifications which are intended to be encompassed by the present disclosure.

Figure 5:
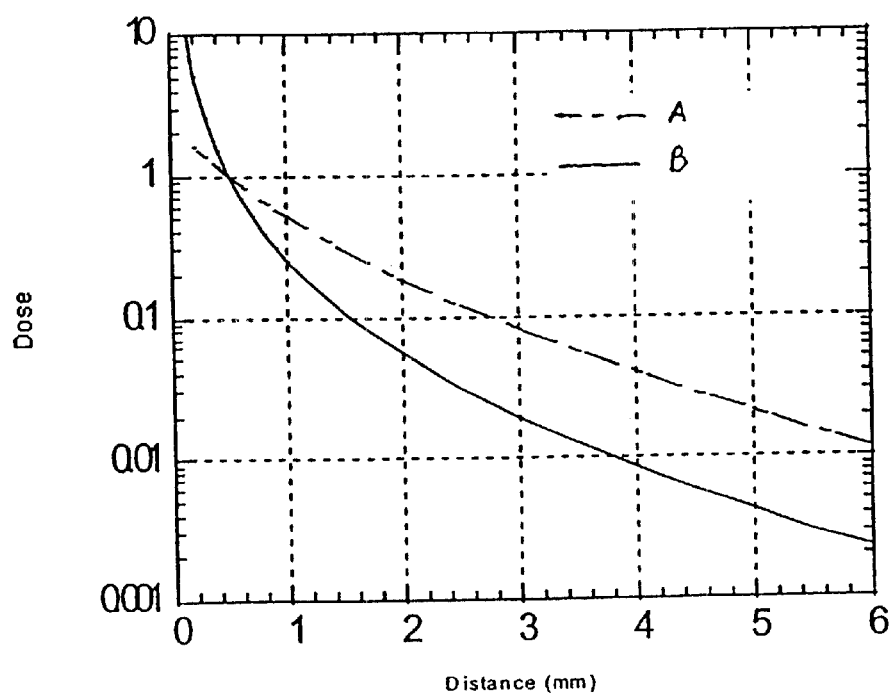
FIG. 5 is a graph comparing radiation dose distributions observed using a directly implanted device and a spheroidal device according to the present invention.

FIG. 5 is a graph comparing a radiation dose distribution observed after implanting a prior art radioactive seed (B) to a radiation dose distribution observed after implanting a device according to an embodiment of the present invention (A). A prior art radioactive iodine-125 seed in which the radioactive iodine-125 was encapsulated within a thin-wall titanium capsule and placed directly in contact with tissue (B), and the resulting radiation dose distribution was compared to a radiation dose distribution from the same seed encapsulated in a silicone outer layer with a radius of 5 millimeters. Measurements were made using thermoluminescent dosimeters in a plastic dosimetry phantom with properties closely approximating soft tissue.

As indicated in FIG. 5, the dose distribution observed for the prior art radioactive seed is highly non-uniform, varying by nearly four orders of magnitude over a distance of 6 cm. In contrast, the dose distribution observed for the embodiment of the present invention is substantially more uniform.

The present invention has been disclosed in connection with the embodiments shown and described in detail above. Various modifications and improvements thereon will, however, become readily apparent to those of ordinary skill in the art from the above description. For example, while the preferred embodiment has been described in the context of treating tumors in breast tissue, the present invention can be used to treat any type of tumor in any type of living tissue. The above description should therefore be considered only as illustrative, and not as limiting, of the present invention. The spirit and scope of the present invention is to be limited only by the following claims.

All patents, publications, and other references cited herein are hereby incorporated by reference in their entirety.

We claim:

1. A device for delivering radiation to tissue adjacent a cavity wall, comprising
    an elastic outer portion having a size sufficient to substantially occupy a volume of a cavity in a patient, and
    a radioactive source encapsulated by the outer portion for delivering radiation therapy to the tissue adjacent the cavity wall;
    wherein the outer elastic portion has relatively low radiation absorptivity.

2. A device as set forth in claim 1, wherein the device has a spheroidal shape.

3. A device as set forth in claim 1, wherein the outer portion is substantially biocompatible.

4. A device as set forth in claim 3, wherein the outer portion is elastic, whereby the outer portion conforms along a contour of the cavity wall.

5. A device as set forth in claim 3, wherein the outer portion comprises a silicone polymer.

6. A device as set forth in claim 3, wherein the outer portion comprises an organic polymer.

7. A device as set forth in claim 6, wherein the organic polymer is substantially biodegradable.

8. A device as set forth in claim 6, wherein the organic polymer is substantially non-biodegradable.

9. A device as set forth in claim 1, wherein the radioactive source comprises a radioactive nuclide which undergoes electron capture decay substantially without emitting beta particles.

10. A device as set forth in claim 9, wherein the radioactive nuclide emits X-rays having energies having a weighted average energy between about 20 keV and about 100 keV.

11. A device as set forth in claim 1, wherein the radioactive nuclide is selected from the group comprising Pd-103, I-125, Gd-153, Sm-145, and Y-169.

12. A device as set forth in claim 1, wherein the radioactive source is substantially centrally located within the outer portion.

13. A method for delivery of radiation to tissue adjacent a cavity wall, comprising identifying a cavity within a body of tissue, the cavity defined by a cavity wall, and disposing within the cavity a device having a radioactive source encapsulated by an elastic outer-portion having relatively low radiation absorptivity and a size sufficient for implantation adjacent the cavity wall, whereby radiation is delivered to the tissue adjacent the cavity wall.

14. A method as set forth in claim 13, wherein identifying a cavity includes removing a volume of tissue from a body of tissue to generate a cavity.

15. A method as set forth in claim 14, wherein removing a volume of tissue includes removing tumorous tissue.

16. A method as set forth in claim 13, wherein disposing a device includes disposing a device having a size substantially the same as the size of the cavity.

17. A method as set forth in claim 16, whereby the device includes a shape conforming to that of the cavity and is substantially in contact with the cavity wall.

18. A device for delivering radiation to tissue adjacent a cavity wall, comprising an elastic outer portion having relatively low radiation absorptivity and a size sufficient to substantially occupy a cavity in need of radiation treatment, and a non-radioactive precursor isotope encapsulated by the outer portion for delivering radiation therapy to the tissue adjacent the cavity wall, whereby thermal neutron activation of the device activates the non-radioactive precursor isotope to a radioactive source.

19. A device as set forth in claim 18, wherein the device has a spheroidal shape.

20. A device as set forth in claim 18, wherein the outer portion is substantially biocompatible.

21. A device as set forth in claim 20, wherein the outer portion has a low radiation absorptivity.

22. A device as set forth in claim 20, wherein the outer portion is elastic, whereby the outer portion conforms along a contour of the cavity wall.

23. A device as set forth in claim 20, wherein the outer portion comprises a silicone polymer.

24. A device as set forth in claim 20, wherein the outer portion comprises an organic polymer.

25. A device as set forth in claim 24, wherein the organic polymer is substantially biodegradable.

26. A device as set forth in claim 24, wherein the organic polymer is substantially non-biodegradable.

27. A device as set forth in claim 18, wherein the radioactive source comprises a radioactive nuclide which undergoes electron capture decay.

28. A device as set forth in claim 27, wherein the radioactive nuclide emits X-rays having energies having a weighted average energy between about 20 keV and about 100 keV.

29. A device as set forth in claim 18, wherein the radioactive nuclide is selected from the group comprising Pd-103, I-124, Gd-153, Sm-145, and Y-169.

30. A device as set forth in claim 18, wherein the radioactive source is substantially centrally located within the outer portion.

* * * * *